United States Patent
Koehler et al.

(10) Patent No.: US 8,861,674 B2
(45) Date of Patent: Oct. 14, 2014

(54) COMPUTED TOMOGRAPHY APPARATUS

(75) Inventors: Thomas Koehler, Norderstedt (DE); Roland Proksa, Neu Wulmstorf (DE); Ewald Roessl, Ellerau (DE)

(73) Assignee: Koninklijke Philips N.V., Eindhoven (NL)

(*) Notice: Subject to any disclaimer, the term of this patent is extended or adjusted under 35 U.S.C. 154(b) by 243 days.

(21) Appl. No.: 13/509,840

(22) PCT Filed: Dec. 10, 2010

(86) PCT No.: PCT/IB2010/055712
§ 371 (c)(1),
(2), (4) Date: May 15, 2012

(87) PCT Pub. No.: WO2011/073863
PCT Pub. Date: Jun. 23, 2011

(65) Prior Publication Data
US 2012/0250821 A1    Oct. 4, 2012

(30) Foreign Application Priority Data
Dec. 15, 2009    (EP) .................................... 09179186

(51) Int. Cl.
*A61B 6/00* (2006.01)
*A61B 6/03* (2006.01)
*G01N 23/04* (2006.01)
*G06T 11/00* (2006.01)

(52) U.S. Cl.
CPC ................. *A61B 6/032* (2013.01); *A61B 6/469* (2013.01); *A61B 6/542* (2013.01); *G01N 23/046* (2013.01); *G06T 11/005* (2013.01); *Y10S 378/901* (2013.01)
USPC ............................................. 378/4; 378/901

(58) Field of Classification Search
CPC .......... A61B 6/032; A61B 6/542; A61B 6/00; G06T 11/005; G01N 23/04; G01N 23/046; G01N 23/06
USPC .............................. 378/4, 15, 16, 62, 91, 901
See application file for complete search history.

(56) References Cited

U.S. PATENT DOCUMENTS

| 5,625,662 | A | 4/1997 | Toth et al. |
| 5,696,807 | A | 12/1997 | Hsieh |

(Continued)

OTHER PUBLICATIONS

Kachelriess, M., et al.; Extended Parallel Backprojection (EPBP) for Arbitrary Cone Angle and Arbitrary Pitch 3D and Phase-Correlated 4D CT Reconstruction; 2004; Med. Phys.; 31:1623-1641.
Kachelriess, M., et al.; Advanced single-slice rebinning in cone-beam spiral CT; 2000; Med. Phys.; 27:754-772.
Stierstorfer, K., et al.; Weighted FBP—a simple approximate 3D FBP algorithm for multislice spiral CT with good dose usage for arbitrary pitch; 2004; Phys. Med. Biol.; 49(11)abstract.

(Continued)

*Primary Examiner* — Jurie Yun

(57) ABSTRACT

The invention relates to a computed tomography apparatus for imaging an object. The computed tomography apparatus comprises a radiation source (2) for generating modulated radiation (4) traversing the object and a detector (6) for generating detection values depending on the radiation (4) after having traversed the object, while the radiation source (2) and the object are moved relative to each other. A weight providing unit (14) provides modulation weights for weighting the detection values depending on the modulation of the radiation (4) and a reconstruction unit (15) reconstructs an image of the object, wherein the detection values are weighted based on the provided modulation weights and an image of the object is reconstructed from the weighted detection values. This can allow to optimize the dose application to the object by modulating the radiation accordingly, wherein the reconstructed images still have a high quality.

20 Claims, 6 Drawing Sheets

(56) References Cited

U.S. PATENT DOCUMENTS

| | | |
|---|---|---|
| 7,532,702 B2 | 5/2009 | Hsieh et al. |
| 7,558,364 B2 | 7/2009 | Lin |
| 2004/0076265 A1 | 4/2004 | Heuscher et al. |
| 2005/0089135 A1 | 4/2005 | Toth et al. |
| 2007/0147579 A1 | 6/2007 | De Man et al. |
| 2009/0252286 A1 | 10/2009 | Mukumoto et al. |

OTHER PUBLICATIONS

Taguchi, K., et al.; A new weighting scheme for cone-beam helical CT to reduce the image noise; 2004; Physics in Medicine and Biology; 49(11)abstract.

Zeng, K., et al.; Correction of Iterative Reconstruction Artifacts in Helical Cone-Beam CT; 2009; 10th International Meeting on Fully Three-Dimensional Image Reconstruction in Radiology and Nuclear Medicine; pp. 242-245.

COMPUTED TOMOGRAPHY APPARATUS

FIELD OF THE INVENTION

The invention relates to a computed tomography apparatus, a computed tomography method and a computed tomography computer program for imaging an object. The invention relates further to an imaging apparatus, an imaging method and an imaging computer program for generating an image of an object.

BACKGROUND OF THE INVENTION

US 2007/0147579 A1 discloses a computed tomography apparatus comprising an X-ray source for generating X-rays which traverse an imaging region. The computed tomography apparatus further comprises a detector for generating detection values depending on the X-rays after having traversed the imaging region. The X-ray source is rotated around the imaging region for allowing the X-rays to traverse the imaging region in different directions. The intensity of the X-rays is modulated as a function of time such that sensitive organs like eyes of a person are irradiated with a minimum dose required to provide an image with a desired noise variance. This reduces the overall dose applied to a person and, in particular, the dose applied to sensitive organs.

However, the varying intensity of the X-rays as function of time leads to image artifacts, thereby decreasing the quality of the reconstructed images.

SUMMARY OF THE INVENTION

It is an object of the present invention to provide a computed tomography apparatus, a computed tomography method and a computed tomography computer program for imaging an object, which allow to improve the quality of reconstructed images which are reconstructed from detection values which have been generated depending on modulated radiation. It is a further object of the present invention to provide a corresponding imaging apparatus, imaging method and imaging computer program for generating an image of an object.

In a first aspect of the present invention a computed tomography apparatus for imaging an object is presented, wherein the computed tomography apparatus comprises:

an imaging region for receiving the object to be imaged, a radiation source for generating modulated radiation traversing the object in the imaging region, a detector for generating detection values depending on the radiation after having traversed the object, a moving unit for moving the radiation source and the object relative to each other, while generating the detection values, for generating detection values depending on radiation having traversed the object in different directions, a weight providing unit for providing modulation weights for weighting the detection values depending on the modulation of the radiation, a reconstruction unit for reconstructing an image of the object, wherein the reconstruction unit is adapted to weight the detection values based on the provided modulation weights and to reconstruct the image of the object from the weighted detection values.

Since the weight providing unit provides modulation weights for the detection values depending on the modulation of the radiation and since the reconstruction unit weights the detection values based on the provided modulation weights, the detection values can be processed depending on the modulation of the radiation in a simple way. The modulation weights can be adapted such that image artifacts in images reconstructed from the weighted detection values are reduced. For example, analytically or by calibration measurements it can be determined which modulation weights depending on the modulated radiation yield a reduction of image artifacts, wherein the accordingly weighted detection values can be used to reconstruct images with reduced image artifacts. In particular, the imaging region, the radiation source and the moving unit can be adapted to modulate the radiation in such a way that the dose applied to more radiation sensitive regions of the object is reduced in comparison to the dose applied to less radiation sensitive regions of the object. In the prior art such a dose modulation leads to image artifacts. However, the weight providing unit and the reconstruction unit can account for the modulated radiation such that image artifacts are reduced. The computed tomography apparatus can therefore allow to optimize the dose application to the object by modulating the radiation accordingly and at the same time to improve the quality of the reconstructed images by providing weights for the detection values depending on the modulation of the radiation.

The radiation source is preferentially an X-ray source. But, the radiation source can also be adapted to generate another kind of radiation like electromagnetic radiation in another wavelength range, ultrasound radiation, nuclear radiation et cetera.

The object is preferentially a person, i.e. the object to be imaged is, for example, an entire person or a part of a person like an organ of a person. The object can also be an animal or a part of an animal or a technical object.

The moving unit is preferentially adapted to rotate the radiation source around the imaging region, while generating the detection values. At the same time an object table on which the object is to be placed can be moved linearly along a rotational axis of the rotating movement of the radiation source with respect to the imaging region for moving the radiation source and the object relative to each other along a helical path. If the object table is not moved, the radiation source and the object are moved relative to each other along a circular path. It is also possible that the radiation source is not moved, but that only the object is moved.

The weight providing unit can be adapted to determine, in particular, calculate, the modulation weights depending on the modulation of the radiation, or the weight providing unit can comprise a storing unit for storing assignments between modulation weights and the intensity of the radiation in tabular or functional form, wherein these assignments can be used for providing the modulation weights.

The reconstruction unit is preferentially adapted to weight the detection values based on the provided modulation weights and to reconstruct an image of the imaging region, i.e. an image of the object located within the imaging region, from the weighted detection values by using a back projection technique. However, the reconstructing unit can also be adapted to reconstruct an image of the imaging region using another reconstruction technique like a reconstructing technique based on Radon inversion.

It is further preferred that the computed tomography apparatus comprises an object table on which the object is to be located, wherein the moving unit is adapted to rotate the radiation source around the object table and wherein the radiation source is adapted such that the intensity of the radiation is lower above the object table than below the object table. The intensity of the radiation is therefore reduced, if the radiation source irradiates the object directly, and the intensity of the radiation is increased, if the object is indirectly irradiated through the object table. This also can lead to a reduced dose applied to the object.

The radiation source is preferentially an X-ray tube and the intensity of the radiation source is preferentially modulated by modulating the tube current of the X-ray tube.

It is further preferred that the weight providing unit is adapted to determine a noise variance of a detection value and to provide the modulation weight for the detection value depending on the inverse noise variance. Thus, in an embodiment for all or for a part of the detection values a noise variance is determined and the modulation weights for the detection values are provided depending on the determined respective inverse noise variance. This weighting of the detecting values with these modulation weights depending on the noise variance allows to improve the noise characteristics of reconstructed images. In particular, the noise within the reconstructed images can be more homogenously distributed and/or can be reduced by weighting the detection values with the inverse noise variance. The noise variance of a detection value is preferentially an estimated variance of the detection value, wherein the estimation is preferentially based on a Poisson model.

It is further preferred that the radiation source is adapted to modulate the intensity of the generated radiation, wherein the weight providing unit is adapted to determine a modulation weight for a detection value depending on the modulated intensity of the generated radiation. Also this allows to improve the noise characteristics of a reconstructed image, in particular, to distribute the noise more homogenously and/or to reduce the noise of the reconstructed image. Preferentially, the weight providing unit is adapted to provide modulation weights which are proportional to the modulated intensity of the generated radiation.

It is further preferred that the radiation source, the detector and the moving unit are adapted to detect redundant detection values being redundant with respect to a same area of the imaging region, wherein, for reconstructing the same area of the imaging region, the reconstruction unit is adapted to:

normalize the modulation weights provided for the redundant detection values, weight the redundant detection values with the normalized modulation weights, reconstruct the same area of the imaging region from the weighted redundant detection values. In a preferred embodiment, the reconstruction unit is adapted to normalize the modulation weights provided for the redundant detection values, which are redundant with respect to the same area of the object, such that the sum of these modulation weights is one. By using redundant detection values the signal-to-noise ratio of the reconstructed image can be improved, wherein the normalization of the respective modulation weights can ensure that the redundancy does not generate image artifacts. An area of the object is, for example, a voxel or a group of voxels of the object in the imaging region.

Redundant detection values are detection values which have been generated at different times, while the radiation, on which the respective detection value depends, has travelled through the object along the same or a similar way in possibly different directions.

It is further preferred that the radiation source is adapted to generate the modulated radiation such that the modulated radiation is conical, wherein the weight providing unit is further adapted to provide coneweights for weighting the detection values depending on a cone angle of the radiation on which the respective detection values depend. Preferentially, detection values belonging to a larger cone angle receive a smaller coneweight than detection values belonging to a smaller cone angle. Since detection values which belong to a larger cone angle cause generally more pronounced cone-beam artifacts than detection values corresponding to a smaller cone angle, by providing larger coneweights for detection values having a smaller cone angle than detection values having a larger cone angle, cone-beam artifacts can be reduced.

The cone angle of a radiation beam on which a respective detection value depends is defined by the angle between the radiation beam and a plane perpendicular to the rotational axis of the computed tomography apparatus. The cone angle could also be regarded as an aperture.

Also coneweights for redundant detection values, which are redundant with respect to the same area of the object, are preferentially normalized as described above with reference to the modulation weights.

It is further preferred that the weight providing unit provides coneweights for the detection values depending on the cone angle such that the coneweights of the detection values continuously and monotonically approach zero with increasing cone angle. This allows avoiding non-continuity of the coneweights as a function of time, thereby suppressing motion artifacts. For example, in particular, if the detection values are redundant detection values and if the corresponding coneweights are normalized, this coneweighting function ensures that the contribution of a projection to the reconstruction results continuously fades out as the projected voxel position approaches the border of the detector panel. This continuous out-fading corresponds to a continuous in-fading of redundant detection values, if the sum of coneweights for all redundant detection values of a voxel is enforced to be one. By this, it is ensured that the weighting of detection values is a continuous function of time as well, because the projected voxel position depends continuously on the projection angle and thus on time. By avoiding any non-continuity of the coneweights as a function of time, motion artifacts are suppressed.

Monotonically approaching zero means that the coneweights are constant or decrease with increasing cone angle, but they do not increase with increasing cone angle.

A voxel of an image is preferentially a three-dimensional image element of the image, wherein the image is comprised of a plurality of voxels.

A projection is preferentially defined as a group of detection values, which have been acquired at the same time while the radiation source was arranged at the same location.

It is further preferred that the radiation source is adapted to generate the modulated radiation such that the modulated radiation is divergent, wherein the computed tomography apparatus further comprises a rebinning unit for rebinning the detection values being generated depending on the divergent radiation thereby forming rebinned projections, wherein the weight providing unit is adapted to:

determine intermediate modulation weights for at least a part of the detection values of a rebinned projection, wherein the intermediate modulation weights depend on the modulation of the radiation, determine for the rebinned projection a mean modulation weight being an average of the intermediate modulation weights for the at least a part of the rebinned detection values of the rebinned projection, wherein the mean modulation weight is the provided modulation weight for the detection values of the rebinned projection. A divergent radiation is preferentially a conical radiation. The mean modulation weight can be an average of the intermediate modulation weights of all rebinned detection values of a rebinned projection or of only a part of the rebinned detection values of a rebinned projection. The rebinning reduces the computational costs for further processing the detection values, for example, for reconstructing an image of the object from the detection values.

In the process of rebinning, the acquired detection values are resorted, or in other words, re-grouped. The natural grouping of detection values coincides with the detection system, i.e., all detection values acquired at the same time with a two-dimensional detector are grouped together. This group is traditionally called a projection. However, for reconstruction, it is more convenient to form different groups of detection values. In particular, it is convenient to put all detection values, which are a) parallel in the projection onto a xy-plane being perpendicular to the rotational axis of the computed tomography apparatus and b) not farther than one fan-angle worth of gantry rotation apart from each other into one group. This group is called a wedge or rebinned projection.

It is further preferred that the moving unit is adapted to rotate the radiation source and the imaging region relative to each other around a rotational axis, while generating the detection values, wherein the at least a part of the rebinned detection values of the rebinned projection are rebinned detection values arranged along a line being perpendicular to the rotational axis. Since only the modulation weights for the rebinned detection values arranged along a line being perpendicular to the rotational axis are used for determining the mean modulation weight and since intermediate modulation weights of all rebinned detection values of a rebinned projection are not used for generating the mean modulation weight, computational costs for generating the mean modulation weight are reduced.

In a preferred embodiment, a rebinned detection value of a rebinned projection can be regarded as being detected by a virtual rebinned detector having detector columns and detector rows of detector elements. Preferentially, for the rebinned detection values arranged along a single detector row a mean modulation weight is determined, which is preferentially assigned to each rebinned detection value of the respective rebinned projection as the modulation weight. The rebinned detection values of a detector row are preferentially arranged along a line being perpendicular to the rotational axis.

In the rebinned detector, two coordinates are used to identify detection values. The coordinates correspond to columns and rows of the rebinned detector. The coordinate axis for the detector column is preferentially parallel to the rotational axis of the computed tomography apparatus. The origin is located for every detector column at the position that is related to a cone-angle of zero degrees. The coordinate axis for the detector row is perpendicular to the other axis and has its origin where the rotation axis is projected to.

It is further preferred that the computed tomography apparatus further comprises a region of interest selection unit for selecting a region of interest to be reconstructed, wherein the at least a part of the rebinned detection values is a part of the rebinned detection values which has been generated depending on radiation having traversed the selected region of interest. This ensures that for the modulation weight calculation by averaging, only detection values are considered, which are really required for reconstructing a desired image of the selected region of interest, thereby further reducing the computational costs.

Preferentially, the mean modulation weight is determined by averaging intermediate modulation weights for rebinned detection values of a rebinned detector, which are generated by radiation having traversed the selected region of interest only.

Preferentially, the weight providing unit is further adapted to determine the mean modulation weight by weightedly averaging the intermediate modulation weights for the at least a part of the rebinned detection values, wherein the intermediate modulation weights are weighted during averaging such that intermediate modulation weights of rebinned detection values which depend on radiation having traversed the region of interest more centrally receive a larger weight than intermediate modulation weights of rebinned detection values which depend on radiation having traversed the region of interest more peripherally. This accounts for the fact that more central rays are used more often than peripheral rays during reconstruction of an image. This further improves the quality of the reconstructed image.

It is further preferred that the weight providing unit is adapted to determine the mean modulation weight by weightedly averaging the intermediate modulation weights of the at least a part of the rebinned detection values, wherein the intermediate modulation weights are weighted during averaging depending on the size of an intersection region of the region of interest and the radiation on which the respective rebinned detection value depends. The importance of a ray for the following reconstruction is related to the size of the intersection region. Thus, by weighting the intermediate modulation weights depending on the size of the intersection region, the importance of the respective ray within the region of interest, i.e. of the respective detection value, can be considered. Assigning one mean modulation weight to a rebinned projection simplifies the use of the weights in the reconstruction unit. However, the potential dose saving may be reduced, because each detection value is weighted with a mean weight instead of an individually optimized weight. The preferred calculation of a weighted mean weight takes into account that for the reconstruction of the region of interest, some detection values, namely the most central detection values, are used more often than others. In this sense, these detection values are more important. Weighting the intermediate modulation weights of the more important detection values with a higher weight implies that the reduced dose saving due to the use of an average modulation weight is minimized.

If radiation is considered as one-dimensional ray, then the intersection region is a line representing the ray within the region of interest and the size of the intersection region is the length of the line.

In a further aspect of the present invention an imaging apparatus for generating an image of an object is presented, wherein the imaging apparatus is adapted to process detection values generated by an acquisition unit comprising:

an imaging region for receiving the object to be imaged, a radiation source for generating modulated radiation traversing the object in the imaging region, a detector for generating detection values depending on the radiation after having traversed the object, a moving unit for moving the radiation source and the object relative to each other, while generating the detection values, for generating detection values depending on radiation having traversed the object in different directions, wherein the imaging apparatus comprises:

a weight providing unit for providing modulation weights for weighting the detection values depending on the modulation of the radiation, a reconstruction unit for reconstructing an image of the object, wherein the reconstruction unit is adapted to weight the detection values based on the provided modulation weights and to reconstruct the image of the object from the weighted detection values.

In a further aspect of the present invention a computed tomography method for imaging an object is presented, wherein the computed tomography method comprises following steps:

generating modulated radiation traversing an object in an imaging region by a radiation source, generating detection values depending on the radiation after having traversed the object by a detector, moving the radiation source and the object relative to each other, while generating the detection values, for generating detection values depending on radiation having traversed the object in different directions by a moving unit, providing weights for the detection values depending on the modulation of the radiation by a weight providing unit, weighting the detection values based on the provided modulation weights by a reconstruction unit, reconstructing an image of the object from the weight detection values by the reconstruction unit.

In a further aspect of the present invention an imaging method for generating an image of an object is presented, wherein the imaging method is adapted to process detection values generated by an acquisition unit comprising:

an imaging region for receiving the object to be imaged, a radiation source for generating modulated radiation traversing the object in the imaging region, a detector for generating detection values depending on the radiation after having traversed the object, a moving unit for moving the radiation source and the object relative to each other, while generating the detection values, for generating detection values depending on radiation having traversed the object in different directions, wherein the imaging method comprises following steps:

providing weights for the detection values depending on the modulation of the radiation by a weight providing unit, weighting the detection values based on the provided modulation weights by a reconstruction unit, reconstructing an image of the object from the weight detection values by the reconstruction unit.

In a further aspect of the present invention the computed tomography computer program comprising program code means for causing a computed tomography apparatus as defined in claim 1 to carry out the steps of the computed tomography method as defined in claim 12, when the computed tomography computer program is run on a computer controlling the computed tomography apparatus.

In a further aspect of the present invention an imaging computer program comprising program code means for causing an imaging apparatus as defined in claim 11 to carry out the steps of the imaging method as defined in claim 13, when the imaging computer program is run on a computer controlling the imaging apparatus.

It shall be understood that the computed tomography apparatus of claim 1, the imaging apparatus of claim 11, the computed tomography method of claim 12, the imaging method of claim 13, the computed tomography computer program of claim 14 and the imaging computer program of claim 15 have similar and/or identical preferred embodiments as defined in the dependent claims.

It shall be understood that a preferred embodiment of the invention can also be any combination of the dependent claims with the respective independent claim.

These and other aspects of the invention will be apparent from and elucidated with reference to the embodiments described hereinafter.

DETAILED DESCRIPTION OF EMBODIMENTS

Figure 1:
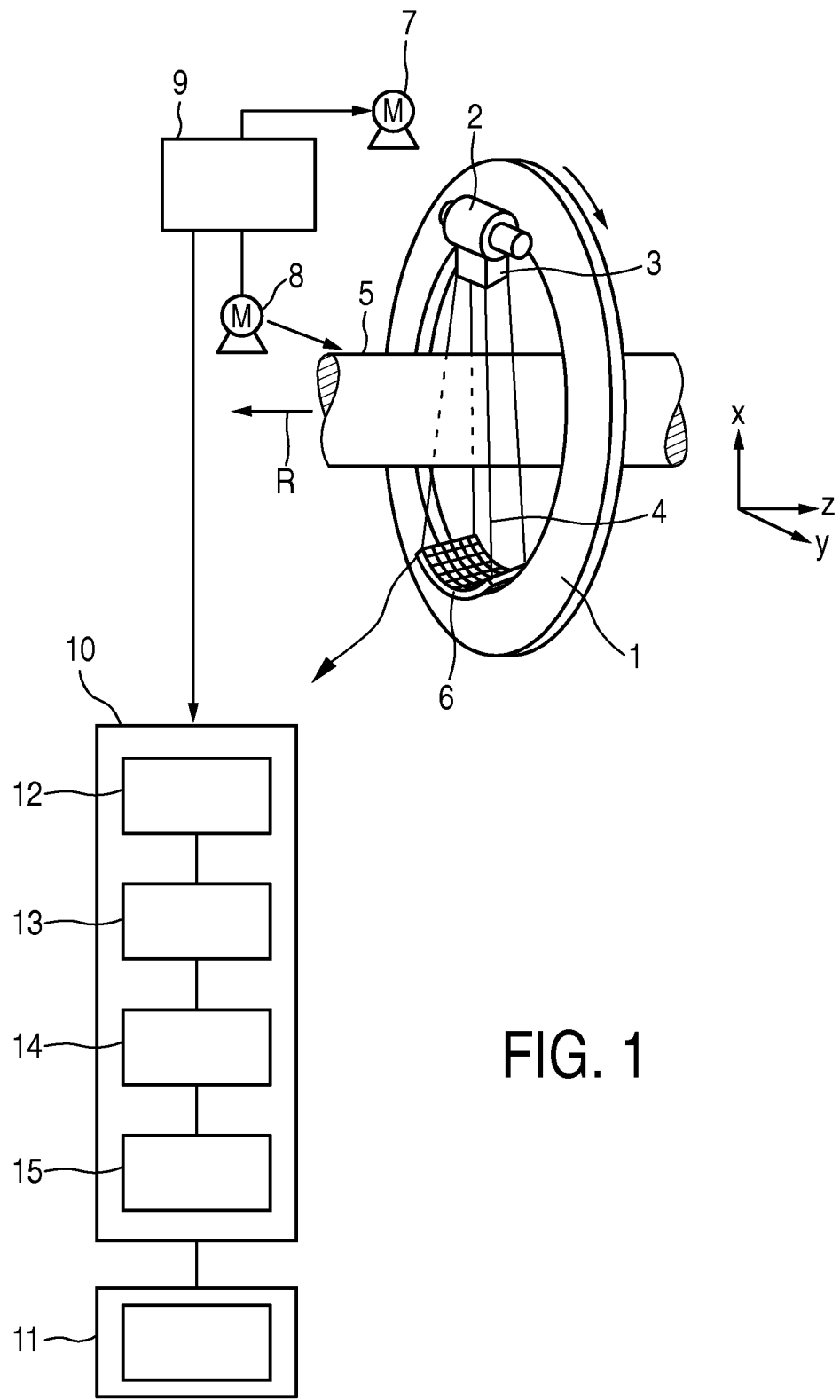
FIG. 1 shows schematically and exemplarily a computed tomography apparatus.

FIG. 1 shows schematically and exemplarily a computed tomography apparatus including a gantry 1 which is capable of rotation about a rotational axis R which extends parallel to a z axis. A radiation source 2, which is, in this embodiment, an x-ray tube, is mounted on the gantry 1. The radiation source 2 is provided with a collimator 3 which forms a conical radiation beam 4 from the radiation generated by the radiation source 2. The radiation traverses an object (not shown) such as a patient in an imaging region 5 which is, in this embodiment, cylindrical. After having traversed the imaging region 5 the conical radiation beam 4 is incident on a detector 6 which comprises a two-dimensional detection surface. The detector 6 is mounted on the gantry 1.

The computed tomography apparatus comprises two motors 7, 8. The gantry 1 is driven at a preferably constant but adjustable angular speed by the motor 7. The motor 8 is provided for displacing the object, for example, a patient, who is arranged on an object table in the imaging region 5, parallel to the direction of the rotational axis R or the z axis. These motors 7, 8 are controlled by a control unit 9, for instance, such that the radiation source 2 and the object move relative to each other along a helical trajectory. However, it is also possible that the object is not moved, but that only the radiation source 2 is rotated, i.e. that the radiation source 2 moves along a circular trajectory relative to the object.

The gantry 1 and the motors 7, 8 can be regarded as a moving unit for moving the radiation source 2 and the object relative to each other along a trajectory, in particular along a circular or helical trajectory.

During a relative movement of the radiation source 2 and the imaging region 5 or the object the detector 6 generates detection values depending on the radiation incident on the detection surface of the detector 6. The radiation source 2 and the detector 6 are moved such that redundant detection values are detected, i.e. e.g. they are moved such that a first detection value is generated by the radiation of a ray of the conical radiation beam traversing the object along a certain path and a second detection value is generated by a ray of the conical radiation beam traversing the object along the same certain path. Detection values, which correspond to the same or similar path through the object and which have been acquired at different times, are regarded as being redundant detection values.

The radiation source is adapted to generate modulated radiation which traverses the imaging region. In this embodiment, the moving unit is adapted to rotate the radiation source around the object table and the radiation source is adapted such that the intensity of the radiation is larger below the object table than above the object table by modulating the tube current of the X-ray source being preferentially the radiation source accordingly. In addition or alternatively, a map of different parts of the object can be provided, wherein the different parts of the object have different sensitivities to radiation dose and wherein the modulation of the radiation depends on the radiation sensitivity of the actually irradiated part of the object. For example, the radiation can be modulated such that a part having a larger radiation sensitivity receives a radiation dose being smaller than a radiation dose received by another part of the object being less radiation sensitive. If, for instance, the object is a person or an animal, the sensitivity to radiation dose is strongly organ-specific. Important organs which are highly dose-sensitive are the eyes, the thyroid, and the female breast. These organs are located at or near the surface of the body and receive therefore a relatively high radiation dose during a computed tomography scan. The radiation is preferentially modulated such that the radiation dose to a superficial organ like the eyes can be reduced, in particular, by tube current modulation, i.e., by reducing the tube current if the radiation source irritates the organ directly.

In this embodiment, the radiation source generates a conical radiation beam and the detector and the moving unit are adapted to detect redundant detection values being redundant with respect to a same area of the imaging region. An area of an imaging region is preferentially a voxel of the object in the imaging region or a group of voxels of the object in the imaging region. In other embodiments, the radiation source can generate radiation having another beam shape, for example, having a fan shape. Moreover, the detector and the moving unit can be adapted to only detect non-redundant detection values.

The detection values, which are, in this embodiment, projection data, are provided to an imaging apparatus 10 for generating an image of the object from the detection values. The imaging apparatus 10 comprises a rebinning unit 12 for rebinning the detection values thereby forming rebinned projections, a region of interest selection unit 13 for selecting a region of interest to be reconstructed and a weight providing unit 14 for providing modulation weights for the detection values depending on the modulation of the radiation. The imaging apparatus 10 further comprises a reconstruction unit 15 for reconstructing an image of the object, wherein the reconstruction unit 15 is adapted to weight the detection values based on the provided modulation weights and to reconstruct the image of the object from the weighted detection values.

The image reconstructed by the reconstruction unit 15 is provided to a display unit 11 for displaying the reconstructed image.

Also the imaging apparatus 10 is preferentially controlled by the control unit 9.

Figure 2:
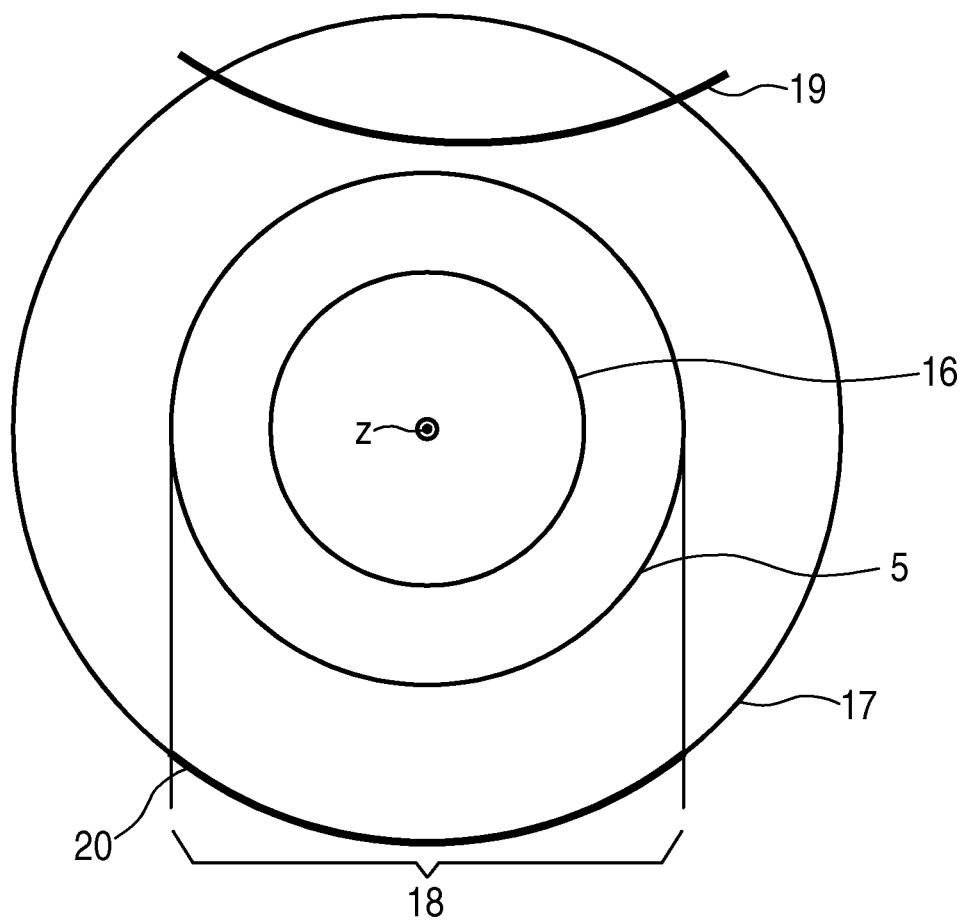
FIGS. 2 to 5 show schematically and exemplarily an extended virtual radiation source and a corresponding virtual detector after acquired detection values have been rebinned.

After the detection values have been rebinned by the rebinning unit 12, a rebinned projection is formed by a virtual extended radiation source 20 generating a virtual wedge comprising radiation over an angular range indicated in FIG. 2 by reference number 18. FIG. 2 shows schematically and exemplarily a region of interest 16, the imaging region 5 and a trajectory 17 viewed in the direction of the z axis. The trajectory 17 along which the radiation source is moved relative to the object is preferentially a circular trajectory or a helical trajectory.

The region of interest selection unit 13 comprises preferentially a user interface which allows a user to select a desired region of interest comprising the object to be reconstructed, which is, for example, a part of a person like an organ of a person. The region of interest selection unit 13 can comprise a graphical user interface together with an input unit like a computer mouse or a keyboard which allows a user to select a desired region of interest.

The weight providing unit 14 can be adapted to determine a noise variance of a detection value and to provide the modulation weight for the detection value depending on the inverse noise variance. The noise variance is preferentially the variance of detection values which can be estimated by using the Poisson model.

Let $I_0$ denote the mean number of photons emitted towards a detector pixel. Due to the attenuation of the beam by the object, only I photons reach the detector pixel on average. Still the number of photons follows the Poisson statistics. Thus, the variance of the detected signal is I. For reconstruction, a so-called line integral through the total attenuation coefficient is estimated by using the formula $$m = \log(I/I_0). \tag{1}$$

The estimated line integral m in accordance with equation (1) can be regarded as a detection value.

For the following discussion, the variance of the derived quantity m is estimated by means of Gaussian error propagation $$\delta m = \frac{\partial}{\partial I} m(I) \delta I = \frac{1}{I} \delta I \tag{2}$$

resulting in $$\mathrm{var}(m) = (\delta m)^2 = \left(\frac{1}{I}\right)^2 (\delta I)^2 = \left(\frac{1}{I}\right)^2 \mathrm{var}(I) = \frac{1}{I} = \frac{1}{\mathrm{var}(I)}. \tag{3}$$

The mean number of photons emitted towards a detector pixel is the intensity of the respective part of the conical radiation beam 4, on which the respective detection value of the detection pixel depends, before traversing the imaging region 5. This intensity or mean number of photons can be determined from air scans. An air scan is an acquisition of detection values without an object present in the imaging region 5.

The weight providing unit 14 can be adapted to provide a modulation weight w being proportional to the inverse variance:

$$w \propto \frac{1}{\mathrm{var}(m)} = \mathrm{var}(I). \tag{4}$$

The variance of the intensity var(I) is equal to the intensity I. Moreover, it can be assumed that the detected intensity of a radiation beam is proportional to the emitted modulated intensity $I_0$ of this radiation beam with a proportional constant $f$. In other words, we can write $$w \propto \mathrm{var}(I) = I = f I_0. \tag{5}$$

The weight providing unit 14 can be therefore adapted to calculate the modulation weights for the detection values depending on the modulated intensity $I_0$ of the generated radiation.

In a preferred embodiment, for a rebinned projection a single modulation weight is determined as will be described in the following.

The weight determination unit 14 is preferentially adapted to determine for a rebinned projection a mean modulation weight as the single modulation weight of the rebinned projection, wherein the mean modulation weight is an average of intermediate modulation weights of at least a part of the rebinned detection values of the rebinned projection. The rebinned detection values of a rebinned projection, which depend on radiation having traversed the selected region of interest, are assigned to different detector rows and detector columns of a rebinned detector 19 and for the rebinned detection values assigned to a single detector row of the rebinned detector 19 of a rebinned projection a mean modulation weight is determined.

Detector columns, i.e. the rebinned detection values along a same detector row, are parameterized by an u-coordinate which is related to the source angle α by $$u=T\sin(\alpha-\alpha_0) \quad (6)$$

where T is the radius of the trajectory of the radiation source and a is the angle of the x-ray source. As disclosed above, all detection values within a rebinned projection are related to lines parallel to each other in the projection to the xy-plane. Thus the rebinned projection can be associated with a projection angle, which is the angle of the projected lines to the xy-plane with the x-axis. This angle is denoted as $\alpha_0$ in the following. This provides a relationship which can be used to assign the proper intermediate modulation weight to rebinned detection values of a detector column, i.e. to a rebinned detection value in a same detector row wherein the rebinned detection value in the same detector row is parameterized by the u-coordinate:

$$w(u) \propto I_0(\alpha_0 + \arcsin(u/T)) \quad (7)$$

where $I_0$ is proportional to the tube current with the source angle as argument. The projection angle of the rebinned detector is $\alpha_0$.

Figure 3:
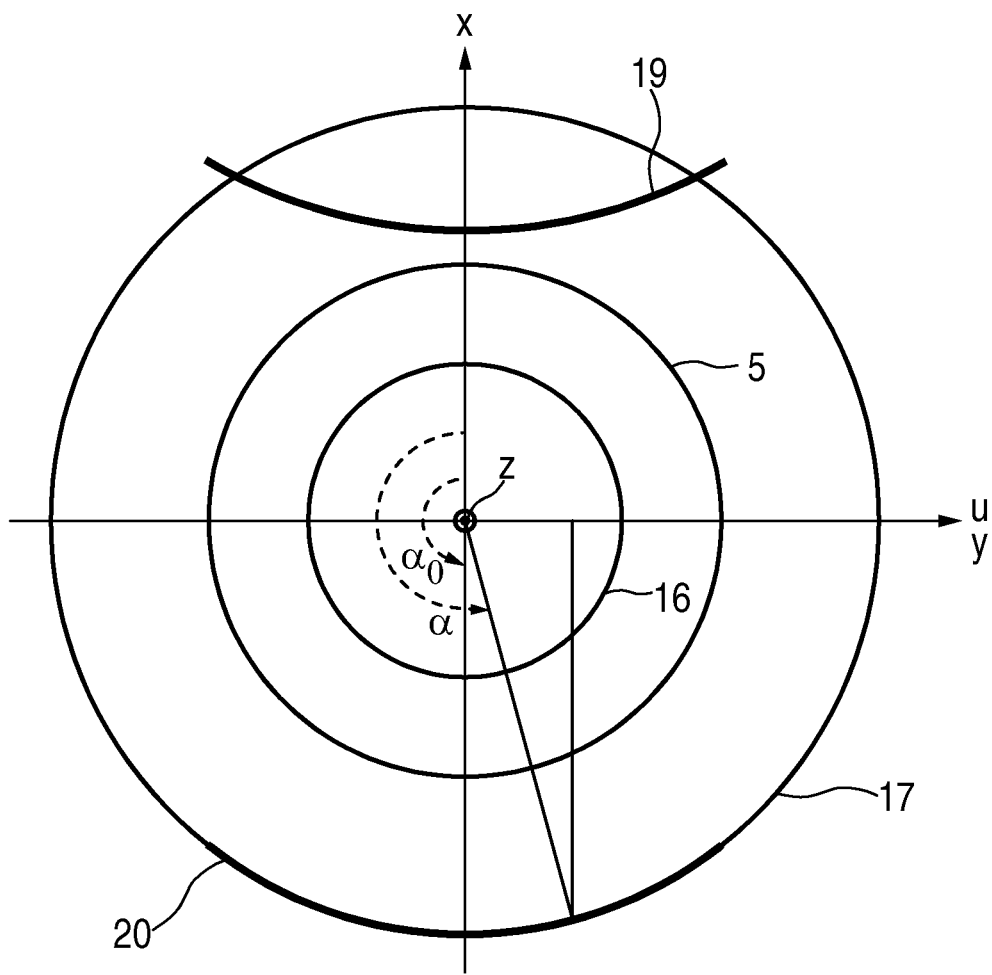

The relationship between the source angle α and the u-coordinate is schematically and exemplarily shown in FIG. 3.

If the selected region of interest requires rebinned detection values along a detector row ranging from $u_{min}$ to $u_{max}$, a mean modulation weight can be determined by averaging intermediate modulation weights for rebinned detection values arranged along a single detector row of the rebinned detector of the rebinned projection defined by the projection angle $\alpha_0$ in accordance with following equation:

$$\overline{w}(\alpha_0) \propto \frac{1}{u_{max} - u_{min}} \int_{u_{min}}^{u_{max}} w(u) du. \quad (8)$$

Figure 4:
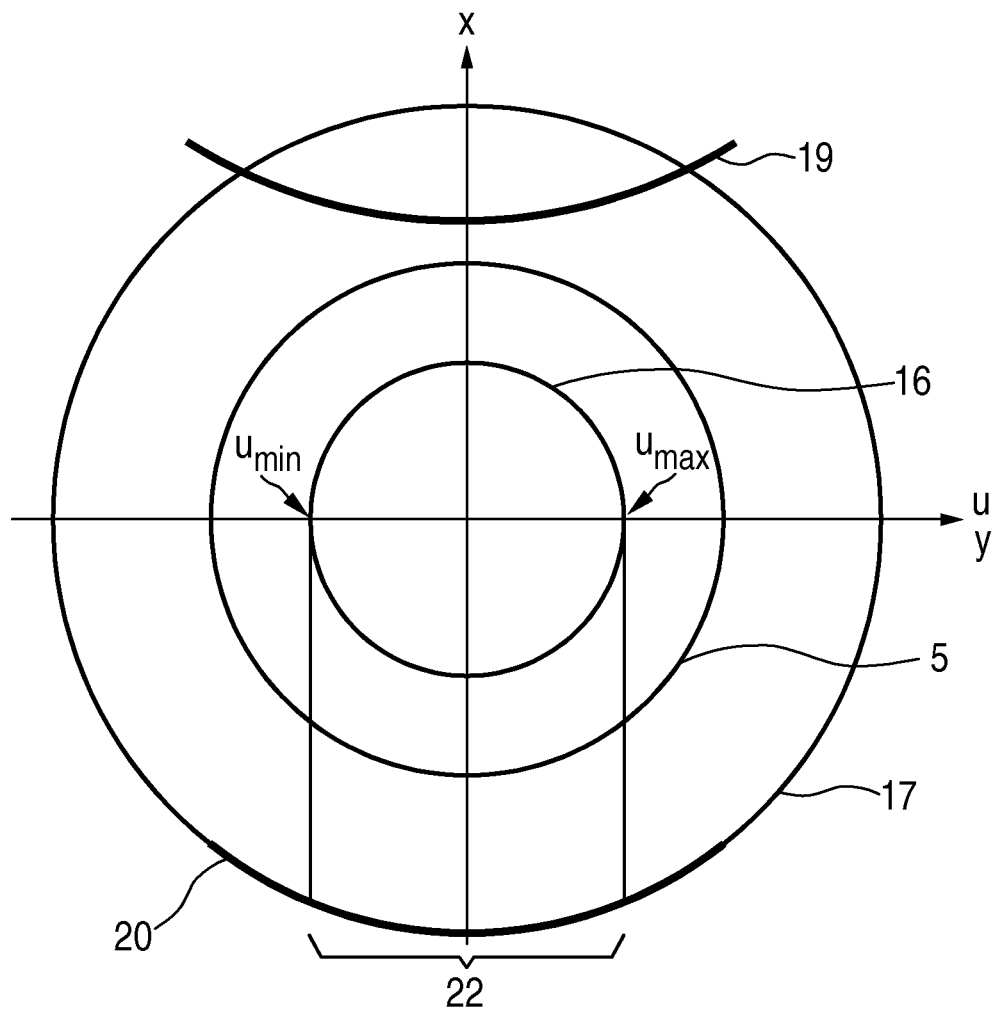

FIG. 4 shows schematically and exemplarily the part 22 of the rebinned rays, i.e. of the corresponding rebinned detection values, which are used for reconstructing an image of the region of interest 16.

However, it is preferred that the intermediate weights are weighted during averaging such that intermediate weights of rebinned detection values which depend on radiation having traversed the region of interest more centrally are larger than intermediate weights of rebinned detection values which depend on radiation having traversed the region of interest more peripherally. This is preferentially achieved by weighting the intermediate weights during averaging depending on the size of an intersection region of the region of interest and the radiation on which the respective rebinned detection value depends. If the radiation on which a rebinned detection value depends is assumed as being a one-dimensional ray, the intersection region is a line representing the ray within the region of interest and the size of the intersection region is the length of the line. The length of such a line and the weighted averaging depending on the ray lengths is illustrated in FIG. 5 and by following equations (9) and (10).

Figure 5:
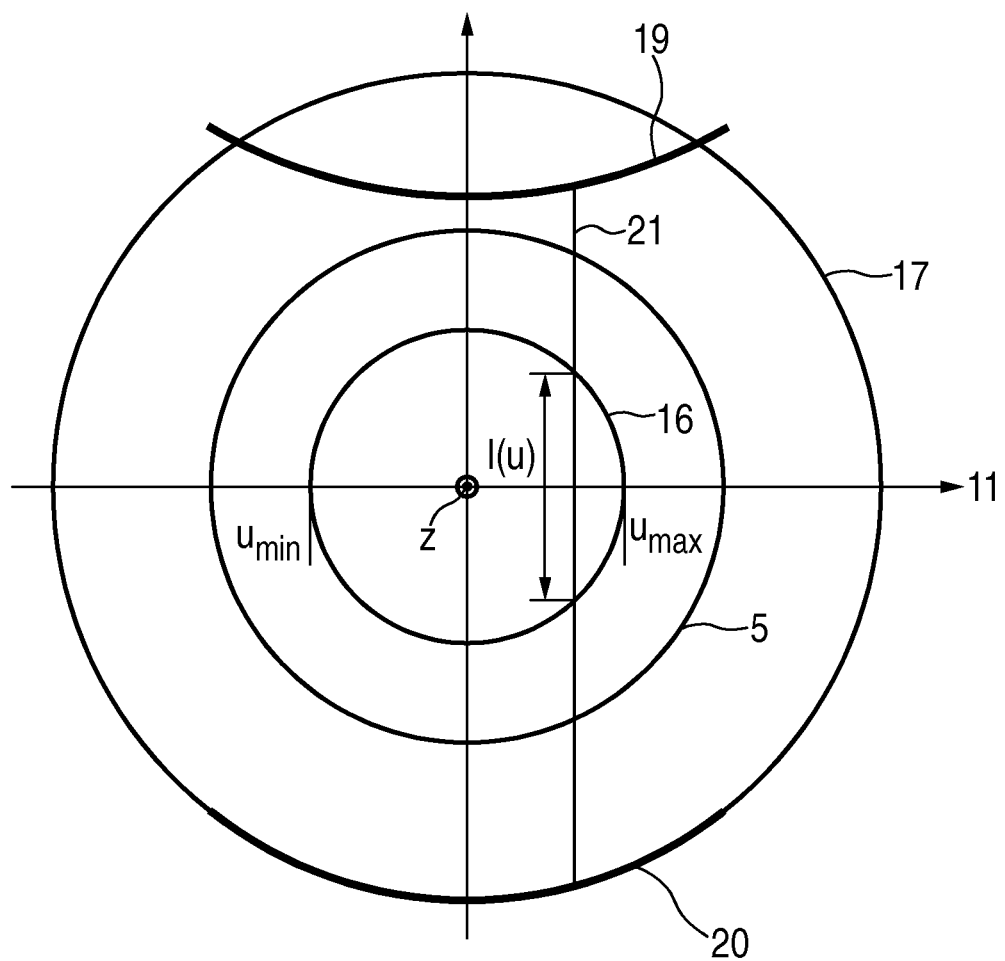

In FIG. 5 a certain ray 21 is shown, on which a rebinned detection value depends. In a preferred embodiment the region of interest 16 is circular and centered with a radius r around the rotational axis z. The length of the ray 21 can then be described by following equation:

$$l(u)=2\sqrt{r^2-u^2}. \quad (9)$$

The mean modulation weight is then preferentially determined according to following equation:

$$\overline{w}(\alpha_0) \propto \frac{\int_{u_{min}}^{u_{max}} l(u)w(u)du}{\int_{u_{min}}^{u_{max}} l(u)du}. \quad (10)$$

Preferentially, to each rebinned detection value of a rebinned projection, the mean modulation weight, which has been determined for this rebinned projection, is assigned.

The weight determination unit is preferentially further adapted to provide coneweights for the detection values depending on a cone angle of the radiation on which the respective detection value depends. Thus, preferentially a modulation weight is provided depending on the modulation of the radiation and a coneweight is provided depending on the cone angle. The weight providing unit can also be adapted to provide further weights which may, for example, depend on a movement signal indicative of a movement of the object. A movement signal is, for example, an electrocardiogram of a heart of a person in cardiac imaging.

The coneweights preferentially continuously and monotonically approach zero with increasing cone angle. The cone-angle is defined as the angle of a ray to a plane that contains the source position and that is furthermore parallel to the xy-plane. Since the coneweights depend on the cone angle which can also be regarded as an aperture, the weight providing unit 14 and the reconstruction unit 15 are preferentially adapted to perform a cone beam weighted or aperture weighted wedge method. The coneweights are preferentially provided such that they follow a weighting function that has its maximum for zero cone angle and which decreases monotonically and continuously to zero, when the cone angle increase and approaches a value which corresponds to the boarder of the detector panel. Practically, a trapezoidal shape can be used as weighting function for defining the coneweights.

The reconstruction unit is preferentially adapted to reconstruct all areas of the region of interest, in particular, all voxels of the region of interest, based on the rebinned detection values and the provided modulation weights and coneweights. For reconstructing an area of the region of interest, modulation weights and coneweights for redundant rebinned detection values, which are redundant with respect to the same area of the region of interest to be reconstructed, are normalized and the rebinned detection values are multiplied with the respective normalized modulation weights and normalized coneweights. The reconstruction unit 15 reconstructs an image of the object by reconstructing areas of the region of interest based on the rebinned detection values, which have been weighted by the normalized modulation weights and normalized coneweights. The reconstruction is preferentially performed by using a back projection technique.

Figure 6:
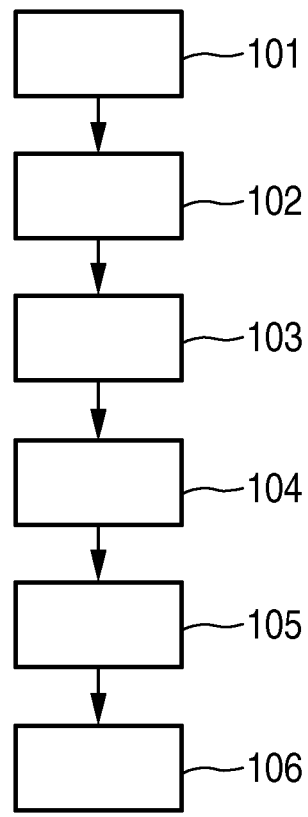
FIG. 6 shows a flowchart exemplarily illustrating a computed tomography method.

In the following a computed tomography method will exemplarily be described with reference to a flowchart shown in FIG. 6.

In step 101, the radiation source 2 rotates around the rotational axis R and the object table with the object is moved in the direction of the rotational axis R to move the radiation source 2 and the object relative to each other along a helical trajectory. The radiation source 2 emits radiation which is collimated to a conical radiation beam by the collimator 3 and which traverses the imaging region 5 of the computed tomography apparatus. The radiation which has traversed the object and the imaging region 5 is detected by the detector 6 which generates detection values depending on the conical radiation beam. The radiation source 2 modulates the intensity of the conical radiation beam preferentially such that the intensity is smaller, if the radiation source is located above the object table, and larger, if the radiation source is located below the object table. The radiation source 2 can also be rotated around the object and the imaging region 5 without moving the object table with the object in the direction of the rotational axis R, in order to move the radiation source 2 and the object relative to each other along a circular trajectory.

In step 102, the detection values are rebinned by the rebinning unit 12 and, in step 103, a region of interest is provided by the region of interest selection unit 13. The region of interest selection unit 13 can provide a predefined region of interest or can allow a user to define a region of interest. A planning image like a scanogram can be provided, wherein the region of interest selection unit 13 can be adapted to allow a user to select a region of interest in the planning image. The planning image is preferentially generated before step 101. In step 104, modulation weights depending on the modulation of the radiation and coneweights depending on the cone angle are provided by the weight providing unit 14, and in step 105 the reconstruction unit 15 reconstructs an image of the object, wherein the detection values are weighted with the modulation weights and coneweights, in particular, multiplied with the normalized modulation weights and normalized the coneweights, and wherein the image of the object is reconstructed from the weighted detection values. The reconstructed image is shown on the display 11 in step 106.

Steps 102 to 106 can be regarded as an imaging method for generating an image of an object based on detection values, which have already been acquired.

The rebinning step 102 can be omitted. Moreover, also the step of providing a region of interest (step 103) can be omitted, wherein, for example, the complete imaging region is regarded as region of interest. In step 105, modulation weights and coneweights for redundant detection values can be normalized, wherein the redundant detection values are weighted with the normalized modulation weights and normalized coneweights and an image of the object is reconstructed from the weighted detection values.

Although in the above described embodiments an analytical reconstruction, in particular, a cone angle weighted or aperture weighted wedge reconstruction is mentioned, the computed tomography apparatus can also be adapted to perform another reconstruction, for example, to perform an iterative reconstruction. If an iterative reconstruction is performed, preferentially a cone angle weighting or aperture weighting is used in order to suppress motion artifacts and to achieve a good convergence behavior. A preferred reconstruction method, which can be used by the reconstruction unit, is, for example, a maximum likelihood iterative reconstruction method as, for instance, disclosed in the article "Correction of Iterative Reconstruction Artifacts in Helical Cone-Beam CT", Zeng, K. et al., 10$^{th}$ International Meeting on Fully Three-Dimensional Image Reconstruction in Radiology and Nuclear Medicine, pages 242-245 can be used. Also the aperture weighted wedge reconstruction method disclosed in "Weighted FBP—a simple approximate 3D FBP algorithm for multislice spiral CT with good dose usage for arbitrary pitch", Stierstorfer K. et al., Phys. Med. Biol., volume 49, pages 2209-2218, 2004 can be used. Furthermore an angular weighted parallel beam back projection as disclosed in, for example, "Extended parallel back projection for standard three-dimensional and phase-correlated four-dimensional axial and spiral cone-beam CT with arbitrary pitch, arbitrary cone-angle, and 100% dose usage", Kachelriess, M. et al., Med. Phys., volume 31, pages 1623-1641, 2004, a weighted cone-beam computed tomography reconstruction method as disclosed in "A new weighting scheme for cone-beam helical CT to reduce the image noise", Taguchi, K. et al., Phys. Med. Biol., volume 49, pages 2351-2364, 2004 or reconstruction methods based on two-dimensional approximations like the ASSR method, which is, for example, disclosed in "Advanced single-slice rebinning in cone-beam spiral CT", Kachelriess, M. et al., Med. Phys., volume 27, pages 754-772, 2000 can be used for reconstructing an image of the examination region.

If redundant detection values and non-redundant detection values have been acquired, for reconstructing an area of the object within the imaging region the reconstruction unit normalizes modulation weights and coneweights of redundant detection values, which are redundant with respect to the same area of the object within the imaging region to be reconstructed, wherein these redundant detection values are weighted with the normalized modulation weights and coneweights. Moreover, the detection values, which are non-redundant with respect to this same area of the object within the imaging region, are weighted with the non-normalized modulation weights and the non-normalized coneweights, and an image of the object is reconstructed from the weighted redundant detection values and the weighted non-redundant detection values.

The modulation weights are preferentially algorithmically used like a cardiac weight in a gated cardiac reconstruction to achieve an improved image quality. However, of course in contrast to a cardiac gated reconstruction, the modulation weight preferentially never becomes zero, but the modulation depth of the modulation weight is preferentially the same as a modulation depth of the tube current, if the radiation source is an X-ray tube.

The cone beam weighting or aperture weighting described above comes preferentially on top of the weighting depending on the modulation of the radiation, in order to be robust with respect to patient motion and in order to reduce cone beam artifacts. The computed tomography apparatus is preferentially used for pediatric scanning.

Although in the above described embodiments the radiation is preferentially modulated such that the intensity of the radiation is smaller, if the radiation source is located above the object table, and larger, if the radiation source is located below the object table, in other embodiments another modulation of the radiation can be provided. For example, a z dose modulation (zDOM) can be used during acquiring the detection values, in particular, if a large detector is used. The idea implemented in zDOM is to use for instance a higher tube current for the shoulders than for the neck. However, for systems with a large cone angle shoulders and neck are over a considerable long period together in the cone and the transition from high tube current for the shoulders to a low tube current for the neck is correspondingly long. As a consequence, voxels in the transition range are reconstructed from projections acquired with different tube currents and the proposed modulation weighting of projections with the actual tube current will decrease the noise level in the images.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Calculations performed by one or several units or devices can be performed by any other number of units or devices. For example, the provision of weights for the detection values, the weighting of the detection values with the weights and the reconstruction based on the weighted detection values performed by the weight providing unit and the reconstruction unit can be performed by a single unit or by any other number of different units. The control of the computed tomography apparatus in accordance with the computed tomography method and/or the control of the imaging apparatus in accordance with the imaging method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a computed tomography apparatus for imaging an object. The computed tomography apparatus comprises a radiation source for generating modulated radiation traversing the object and a detector for generating detection values depending on the radiation after having traversed the object, while the radiation source and the object are moved relative to each other. A weight providing unit provides modulation weights for weighting the detection values depending on the modulation of the radiation and a reconstruction unit reconstructs an image of the object, wherein the detection values are weighted based on the provided modulation weights and an image of the object is reconstructed from the weighted detection values. This can allow to optimize the dose application to the object by modulating the radiation accordingly, wherein the reconstructed images still have a high quality.

The invention claimed is:

1. A computed tomography apparatus for imaging an object, the computed tomography apparatus comprising:
   an imaging region for receiving the object to be imaged,
   a radiation source for generating modulated radiation traversing the object in the imaging region,
   a detector for generating detection values depending on the radiation after having traversed the object,
   a moving unit for moving the radiation source and the object relative to each other, while generating the detection values, for generating detection values depending on radiation having traversed the object in different directions,
   a weight providing unit for providing modulation weights for weighting the detection values depending on the modulation of the radiation,
   a reconstruction unit for reconstructing an image of the object, wherein the reconstruction unit is adapted to weight the detection values based on the provided modulation weights and to reconstruct the image of the object from the weighted detection values.

2. The computed tomography apparatus as defined in claim 1, wherein the computed tomography apparatus comprises an object table on which the object is to be located, wherein the moving unit is adapted to rotate the radiation source around the object table and wherein the radiation source is adapted such that the intensity of the radiation is lower above the object table than below the object table.

3. The computed tomography apparatus as defined in claim 1, wherein the weight providing unit is adapted to determine a noise variance of a detection value and to provide the modulation weight for the detection value depending on an inverse of the noise variance.

4. The computed tomography apparatus as defined in claim 3, wherein the weight providing unit estimates the noise variance using a Poisson model.

5. The computed tomography apparatus as defined in claim 1, wherein the radiation source is adapted to modulate the intensity of the generated radiation, wherein the weight providing unit is adapted to determine a modulation weight for a detection value depending on the modulated intensity of the generated radiation.

6. The computed tomography apparatus as defined in claim 1, wherein the radiation source is adapted to generate the modulated radiation such that the modulated radiation is conical and wherein the weight providing unit is further adapted to provide coneweights for weighting the detection values depending on a cone angle of the radiation on which the respective detection values depend.

7. The computed tomography apparatus as defined in claim 1, wherein the radiation source is adapted to generate the modulated radiation such that the modulated radiation is divergent, wherein the computed tomography apparatus further comprises a rebinning unit for rebinning the detection values being generated depending on the divergent radiation thereby forming rebinned projections, wherein the weight providing unit is adapted to:
   determine intermediate modulation weights for at least a part of the detection values of a rebinned projection, wherein the intermediate modulation weights depend on the modulation of the radiation,
   determine for the rebinned projection a mean modulation weight being an average of the intermediate modulation weights for the at least a part of the rebinned detection values of the rebinned projection, wherein the mean modulation weight is the provided modulation weight for the detection values of the rebinned projection.

8. The computed tomography apparatus as defined in claim 7, wherein the moving unit is adapted to rotate the radiation source and the imaging region relative to each other around a rotational axis, while generating the detection values, wherein the at least a part of the rebinned detection values of the rebinned projection are rebinned detection values arranged along a line being perpendicular to the rotational axis.

9. The computed tomography apparatus as defined in claim 7, wherein the computed tomography apparatus further comprises a region of interest selection unit for selecting a region of interest to be reconstructed, wherein the at least a part of the rebinned detection values is a part of the rebinned detection values which has been generated depending on radiation having traversed the selected region of interest.

10. The computed tomography apparatus as defined in claim 9, wherein the weight providing unit is further adapted to determine the mean modulation weight by weightedly averaging the intermediate modulation weights for the at least a part of the rebinned detection values, wherein the intermediate modulation weights are weighted during averaging such that intermediate modulation weights of rebinned detection values which depend on radiation having traversed the region of interest more centrally receive a larger weight than intermediate modulation weights of rebinned detection values which depend on radiation having traversed the region of interest more peripherally.

11. The computed tomography apparatus as defined in claim 9, wherein the weight providing unit is further adapted to determine the mean modulation weight by weightedly averaging the intermediate modulation weights of the at least a part of the rebinned detection values, wherein the intermediate modulation weights are weighted during averaging depending on the size of an intersection region of the region of interest and the radiation on which the respective rebinned detection value depends.

12. The computed tomography apparatus as defined in claim 1, wherein the reconstruction unit normalizes the modulation weights for redundant detection values, creating normalized modulation weights, and weights the redundant detection values with the normalized modulation weights.

13. The computed tomography apparatus as defined in claim 12, wherein the reconstruction unit weights non-redundant detection values with the modulation weights and weights the redundant detection values with the normalized modulation weights.

14. The computed tomography apparatus as defined in claim 1, wherein the detection values include only non-redundant detection values.

15. The computed tomography apparatus as defined in claim 1, wherein the detection values include at least one of non-redundant detection values and redundant detection values, and the reconstruction unit weights the non-redundant detection values with non-normalized modulation weights and weights the redundant detection values with normalized modulation weights.

16. An imaging apparatus for generating an image of an object, the imaging apparatus being adapted to process detection values generated by an acquisition unit comprising:
   an imaging region for receiving the object to be imaged,
   a radiation source for generating modulated radiation traversing the object in the imaging region,
   a detector for generating detection values depending on the radiation after having traversed the object,
   a moving unit for moving the radiation source and the object relative to each other, while generating the detection values, for generating detection values depending on radiation having traversed the object in different directions,
wherein the imaging apparatus comprises:
   a weight providing unit for providing modulation weights for weighting the detection values depending on the modulation of the radiation,
   a reconstruction unit for reconstructing an image of the object, wherein the reconstruction unit is adapted to weight the detection values based on the provided modulation weights and to reconstruct the image of the object from the weighted detection values.

17. A computed tomography method for imaging an object, the computed tomography method comprising following steps:
   generating modulated radiation traversing an object in an imaging region by a radiation source,
   generating detection values depending on the radiation after having traversed the object by a detector,
   moving the radiation source and the object relative to each other, while generating the detection values, for generating detection values depending on radiation having traversed the object in different directions by a moving unit,
   providing modulation weights for the detection values depending on the modulation of the radiation by a weight providing unit,
   weighting the detection values based on the provided modulation weights by a reconstruction unit,
   reconstructing an image of the object from the weighted detection values by the reconstruction unit.

18. A non-transitory computer readable medium comprising program code for causing a computed tomography apparatus to carry out the computed tomography method as claimed in claim 17.

19. An imaging method for generating an image of an object, the imaging method being adapted to process detection values generated by an acquisition unit comprising:
   an imaging region for receiving the object to be imaged,
   a radiation source for generating modulated radiation traversing the object in the imaging region,
   a detector for generating detection values depending on the radiation after having traversed the object,
   a moving unit for moving the radiation source and the object relative to each other, while generating the detection values, for generating detection values depending on radiation having traversed the object in different directions,
wherein the imaging method comprises following steps:
   providing modulation weights for the detection values depending on the modulation of the radiation by a weight providing unit,
   weighting the detection values based on the provided modulation weights by a reconstruction unit,
   reconstructing an image of the object from the weighted detection values by the reconstruction unit.

20. A non-transitory computer readable medium comprising program code for causing an imaging apparatus to carry out the imaging method as claimed in claim 19.

* * * * *